United States Patent
De Lorenzo et al.

(10) Patent No.: US 8,549,938 B2
(45) Date of Patent: Oct. 8, 2013

(54) METHOD FOR THE ELASTIC INSTALLATION OF DETECTION DEVICES ON PIPELINES AND SUITABLE DEVICE THEREFOR

(75) Inventors: Gianpietro De Lorenzo, Segrate (IT); Giuseppe Giunta, San Donato Milanese (IT)

(73) Assignee: ENI S.p.A., Rome (IT)

( * ) Notice: Subject to any disclaimer, the term of this patent is extended or adjusted under 35 U.S.C. 154(b) by 213 days.

(21) Appl. No.: 12/988,892

(22) PCT Filed: Apr. 16, 2009

(86) PCT No.: PCT/EP2009/002978
§ 371 (c)(1),
(2), (4) Date: Jan. 10, 2011

(87) PCT Pub. No.: WO2009/130029
PCT Pub. Date: Oct. 29, 2009

(65) Prior Publication Data
US 2011/0113887 A1    May 19, 2011

(30) Foreign Application Priority Data
Apr. 24, 2008    (IT) .............................. MI2008A0760

(51) Int. Cl.
*G01N 29/24*    (2006.01)
(52) U.S. Cl.
USPC ...................................... 73/866.5; 73/40.5 A
(58) Field of Classification Search
USPC ................ 73/866.5, 622, 627, 628, 629, 632, 73/640, 40.5 A
See application file for complete search history.

(56) References Cited

U.S. PATENT DOCUMENTS

| | | | |
|---|---|---|---|
| 4,144,517 A | | 3/1979 | Baumoel |
| 4,242,744 A | * | 12/1980 | Rottmar ........................ 367/173 |
| 4,286,470 A | * | 9/1981 | Lynnworth ................ 73/861.18 |
| 4,738,737 A | | 4/1988 | Runde et al. |
| 5,131,278 A | | 7/1992 | Baumoel |
| 5,755,136 A | | 5/1998 | Getman et al. |
| 2003/0226412 A1 | * | 12/2003 | Rumminger et al. ......... 73/866.5 |
| 2007/0251314 A1 | | 11/2007 | Molenaar et al. |
| 2012/0103069 A1 | * | 5/2012 | Al-Qahtani et al. ....... 73/40.5 A |

FOREIGN PATENT DOCUMENTS

| | | |
|---|---|---|
| DE | 10 2006 015 217 | 10/2007 |
| EP | 0 769 685 | 4/1997 |
| EP | 0 974 815 | 1/2000 |
| EP | 1 780 518 | 5/2007 |

OTHER PUBLICATIONS

International Search Report issued Aug. 28, 2009 in PCT/EP09/002978 filed Apr. 16, 2009.

* cited by examiner

*Primary Examiner* — Peter Macchiarolo
*Assistant Examiner* — Rose M Miller
(74) *Attorney, Agent, or Firm* — Oblon, Spivak, McClelland, Maier & Neustadt, L.L.P.

(57) ABSTRACT

With a certain pipeline, either buried or deposited on a sea/lake bottom, the formation of critical faults is determined and localized, which arise in the walls of the pipeline, or the development of an already localized fault is monitored, through sensors regularly distributed along the pipeline, and fixed to the same by means of a plate equipped with a pass-through hole in which the sensor is inserted.

9 Claims, 5 Drawing Sheets

METHOD FOR THE ELASTIC INSTALLATION OF DETECTION DEVICES ON PIPELINES AND SUITABLE DEVICE THEREFOR

The present invention relates to a method for the elastic installation of detection devices, particularly a detection device containing a sensor, on pipelines, preferably buried or deposited on sea/lake bottoms and the device suitable for the purpose.

More specifically, the present invention relates to a method for the elastic installation of devices comprising acoustic sensors (acoustic transducers), fiber optic sensors, accelerometers, etc. on pipelines, said sensors being suitable for monitoring the buried pipelines or sealines, e.g. for effecting the remote detection, localization and monitoring of critical faults which arise in said buried pipelines or sea-lines. These pipelines can be used in the transportation of gas or hydrocarbon liquids, such as natural gas (methane), oil or hydrocarbon derivatives of petroleum, or water, fresh or salt water, particularly well production water.

As is known, the transportation of fluids of a fossil nature, such as natural gas or petroleum, by means of pipelines is the simplest and most economical means of transport as it guarantees a continuous flow of the fluid, without substantial interruptions, from the production sites to the consumption/work areas or shipment areas for oversea transportation.

As mentioned above, the transportation of these products through pipelines is only substantially continuous as, for maintenance purposes; the pipelines must be periodically controlled. In other words, as the pipelines are subject to mechanical stress, the flow of fluid is periodically interrupted, or substantially reduced, to allow the operators to introduce suitable devices inside the pipeline for detecting the possible formation of critical faults (for example cracks or corrosion points) and monitoring the development of those previously detected.

These control and monitoring operations of critical faults are fundamental for correctly managing the pipeline as they enable interventions and repairs to be effected on the fault before it causes greater damage to the pipeline.

The risk of the formation of cracks in the material of a pipeline, generally carbon steel, is due to reasons associated with the fluid transported and also to external causes. In the former case, the risk factor is linked to the pressure jumps of the fluid transported which cause radial expansions and contractions of the pipe which, with time, can cause the formation of faults due to fatigue stress. In the latter case, as the pipeline is buried or resting on sea/lake bottoms, these are subject to movement of the earth or sea currents which tend to deform them.

The control and monitoring system of pipelines currently in use has at least one evident drawback, in addition to that previously mentioned with respect to the necessity of interrupting or reducing the flow of fluid transported to allow the introduction and subsequent recovery of control devices. If, in fact, the presence of a fault in the material of the pipeline being examined is discovered, by means of these control devices, this can and will have to be monitored discontinuously, periodically, with the relative stoppages/reductions in the flow of fluid transported inside the pipeline.

An objective of the present invention is to provide a method for the elastic installation on buried or underwater pipelines of sensors, e.g. acoustic sensors capable of perceiving the ultrasounds or the acoustic waves emitted as a result of the formation of critical faults and which are therefore capable of detecting, localizing and monitoring said critical faults when they arise, or are amplified, in said pipelines, without the drawbacks mentioned above and which allow the formation of a critical fault to be safely identified at the moment of its formation and/or with the continuous monitoring of the possible development of the fault, without intervening on the flow-rate of the fluid transported. In this way, an operator can repair the section of pipeline involved when the fault has become such as to endanger the integrity of the pipeline itself.

An object of the present invention therefore relates to a method for the elastic installation on pipelines of a detection device containing a which comprises:

i. arranging a substantially rectangular, steel supporting plate, equipped with a pass-through opening, on the pipeline;
ii. supporting the sensor on the plate, in correspondence with the pass-through opening, together with the associated electronics;
iii. welding one of the two edges of the plate, orthogonal to the axis of the pipeline, onto the same pipeline and withholding the parallel sides, to the axis of the pipeline, of the supporting plate between two overturned L-shaped flanges and welded onto the pipeline in correspondence with the other orthogonal edge;
iv. covering the sensor and the associated electronics with a protection box, equipped with a top, which adapts itself to the plate;
v. positioning a blocking spring between the sensor and the internal top of the box;
vi. fixing the covering box to the supporting plate.

According to the present invention the sensor is a sensor of acoustic waves within the field of ultrasounds.

The supporting plate can be rectangular or square and can have a pass-through opening wherein the sensor is inserted so that it can rest in contact with the metal or the coating of the pipeline. A spring is positioned above the sensor, in order to prevent the sensor from moving during the operation and, therefore, no longer having an adequate contact with the surface of the pipeline, so that when the box is inserted and is fixed to the supporting plate, the spring exerts, through the top of the box, a pressure force which acts on the sensor by keeping it blocked in its original position. The covering box is fixed to the supporting plate by means of screws which are engaged in threaded holes present on the plate itself.

The top of the box can be integral and not separable from the walls of the box or it can be extracted and fixed to the walls of the box, under sealing conditions, by suitable fixing means, for example screws.

The plate is fixed to the pipeline, partially by welding and partially through the overturned L-shaped flanges. The latter are situated (welded only onto the outer surface of the pipeline) so as to keep the plate pressed against the pipe. This arrangement does not allow upward movements of the plate, but only longitudinal sliding movements which follow the elastic deformations of the pipeline, in particular the radial elastic deformations due to sudden changes of pressure of the transported fluid.

According to an alternative method, step (iii), which fastens the supporting plate to the pipeline, can be different, with no welding of the edge and containment in correspondence with the other of the L-shaped flanges. In particular, the edges of the plates orthogonal to the axis of the pipeline can be shaped to respectively receive two belts which are tightened around the pipeline.

In order to avoid an extremely rigid fixing system, at least two spring elements are respectively positioned between the belt and each shaped part of the two edges of the plate, which guarantee that the plate will follow the radial movements of the pipeline when subjected, for example, to the above radial deformations.

For safety reasons, in order to avoid damage to the sensor and/or associated electronics, due to possible escape currents or electric discharges from atmospheric events, it is preferable for the belts not to be metallic but made of electrically non-conductive materials. Belts made of thermoplastic polymers, polyethylene or polypropylene, reinforced with glass and/or Kevlar® fibres, can be used for the purpose.

The detection device containing a sensor, such as an acoustic sensor for detecting the acoustic waves (ultrasounds) associated with the formation/development of critical faults in pipelines, is described in the enclosed claims.

An exemplifying process for the remote detection, localization and monitoring of critical faults in buried or underwater pipelines, by means of acoustic sensors applied on the pipeline with the method and device of the present invention, comprises:
  a. arranging, on the outer surface of the pipeline, a first series of sensors (passive sensors) capable of detecting the emission of acoustic waves within the range of ultrasounds;
  b. detecting, by means of said sensors, the acoustic waves (ultrasounds) distributed along the walls of the pipeline with the formation of a critical fault or at the moment of a development of a fault already under control;
  c. transforming the signals received into electric signals;
  d. transmitting the electric signals coming from the at least two sensors closest to the critical fault, positioned near said fault, to a data collection centre;
  e. transforming each electric signal received into a digital signal sent to a remote processor system, equipped with software, which identifies the reception time of the emitted from the fault, relating to said at least two sensors close to the fault, by a measurement of the acoustic amplitude of the emission;
  f. identifying and/or monitoring, by means of the software, the relative position of the fault that has arisen or that is developing, with respect to said at least two sensors which have revealed the acoustic emission and its distance L (k) from said at least two sensors, starting from that furthest away from the fault, by the development of the relation:

$$L(k) = V_k(s,\tau) \times t$$

wherein $V_k(s,\tau)$ is the propagation rate of the acoustic waves relating to the sensor k of said at least two sensors, depending on the space (s) that the acoustic waves must go through the physical means of the pipeline, the propagation time (t) and the time ($\tau$) associated to the service state of the sensor k.

The term "service state of the sensor" as used in the present description refers to a measurement of the receptive function of the passive sensors, depending on the service time and work conditions. For instance, for the assessment of the service state of the passive sensors, one or more Active Sensors (active acoustic transducers), distributed along the outer surface of the pipeline, can be used, which are capable of emitting, on command, acoustic waves that are comparable with those emitted from a real fault which is formed "ab initio" in the pipeline or which are emitted from a fault already present in the pipeline and which evolves with time. In this way, the periodical activation of said Active Sensors not only allows the service state of the passive sensors to be controlled, but also allows the periodical calibration of the whole monitoring system, object of the present invention.

The identification of the formation of a critical fault or the monitoring of a pre-existing fault can be effected on any type of pipeline even if it is preferable to apply the method, object of the present invention, on buried pipelines or pipelines deposited on sea/lake bottoms, as, once functioning, they are only accessible with programmed recovery and maintenance interventions. Examples of pipes are those made of carbon steel with diameters of up to 150 cm, for example from 10 to 130 cm, possibly coated with protective materials of a plastic nature fixed to the metal by thermowelding or by hot-melt adhesives.

The acoustic sensors can be arranged over the whole length of the pipeline at predefined intervals. For economical reasons, however, it is preferable to arrange them in correspondence with potentially critical sections such as weldings, curves, sections subject to stress due to the ground movement, etc. Once the potentially critical sections have been identified, the sensors are generally arranged over lengths of 800-1500 m of pipeline, at distances from each other of 10 to 50 m, preferably from 20 to 40 m, generally at a distance of 30 m.

The sensors can be arranged in a straight line on the section of pipeline of interest, along a generating line, or around a pipeline according to a substantially helicoidal line. Alternatively, the sensors can be arranged around each of a series of fixed positions spaced linearly from each other.

The distance between each sensor is preferably always the same, as the software takes the distances between the sensors into account in processing the signals.

Any acoustic sensor capable of detection of the diffusion of acoustic waves (ultrasounds) on steel pipes, possibly coated with protective material of a plastic nature, can be used in the method, object of the present invention; even if acoustic sensors of the piezoelectric type are preferred as they are selective for that range of acoustic frequencies (30-600 kHz). Alternative acoustic sensors can be electromagnetic transducers or "magnetostrictive" transducers.

The propagation rate of the acoustic wave resulting from the formation of a critical fault on the pipeline, or from the development of a fault under control, depends on the position in which it is formed, whether superficially, outside the pipeline or inside the pipeline, or in the thickness of the pipe. In any case, the propagation velocity is influenced by the materials, generally by the protection material of the pipeline (in the case of a fault on the outer surface) or by the fluid transported (in the case of a fault on the inner surface). The signals received at least from a first closer sensor and from at least a second more distant sensor, transformed into electric signals in situ, are transmitted to a data collection unit, transformed into digital signals and remotely sent where a process unit processes them to identify their origin, particularly if on the right or left of said at least a first closer sensor and the distance from said at least second more distant sensor.

Once the positions of the sensors along the pipeline and its geometrical characteristics are known, the software effects the following operations:
  1. calculation of the position of the fault;
  2. historical analysis of the dependence of the emission of a fault on forcing actions, such as operative cycles of temperature, pressure, flow, corrosion, etc. and on the time in general; and
  3. calibration of the detection system.

In particular, with each detection cycle, the software allows the determination of the position of the fault and the definition of the statistic relations for its monitoring:
  between the intensity of the acoustic emission and the emission frequency per fault;

between the acoustic emission times and the number of emission events per fault;

between the acoustic emission values per fault and the values of the local parameters of temperature, pressure, flow, precipitation of salts, etc.

between the acoustic emission frequencies per fault and the values of the local parameters of temperature, pressure, flow, precipitation of salts, etc.

between the parameters which define the form of the acoustic signal detected, also called in technical jargon: rise time, peak time, duration time, etc. and the local parameters of temperature, pressure, flow, precipitation of salts, etc.

between the parameters which define the form of the acoustic signal detected, as described above, and the local parameters of temperature, pressure, flow, precipitation of salts, etc.

between the parameters which define the form of the acoustic signal detected, as described above, and the frequencies and times of the emissive events, per fault.

The calculation of the position of a fault is the main action of the software. This depends on the definition, in an acoustic sensor, of the materials which form the pipeline or which flow through it.

A material is generally characterized by two parameters: the acoustic velocity and the acoustic attenuation. The former is the propagation velocity of the elastic waves and is calculated from the propagation time, also called time of flight, i.e. by measuring the time necessary for the sound to go through a certain dimension of the material. The second is a measurement of the loss of energy of the acoustic wave.

The acoustic velocity v, and the attenuation coefficient, $\alpha$, are determined by measuring the time between two successive echoes (time of flight) and their relative amplitudes according to the formulae:

$$v=h/t [m/s]$$

$$\alpha=(h)^{-1}*20 \log_{10}(A1/A0)[dB/\text{meter}]$$

wherein h is the distance between the fault and the active sensors or passive sensors, A0 and A1 are the amplitudes of the two echoes and t is the time of flight calculated as the difference t=t1−t0.

As illustrated above, various sensors are necessary for the present invention. Some of these, called Active Sensors, are used as acoustic wave sources for the calibration phase of the measurement process through passive sensors (receivers). The detections of the acoustic phenomenon induced in the calibration is therefore a complex function of material parameters through which the sound waves pass and, implicitly, of the specific set-up of the single sensor.

If m is the number of Acoustic Sensors with an active functionality and n the number of acoustic sensors with a passive functionality, the calibration process defines the transmission phenomenon between different positions along the pipeline. The application of the analysis process of the signal emitted from the j-th Active Sensor, for j=1, . . . , m, and detected by "n" passive sensors, with m≤n, allows the transmission rate of the acoustic waves to be determined and the attenuation the acoustic signal in relation to cylindrical or Cartesian space coordinates on the surface of the pipeline.

If the "n" distribution functions of the velocities are $v_k(x_j)$, for k=1, . . . n, relating to the positions $x_j$, for j=1, . . . , m, of the calibration emission point, it is therefore possible to position the emission point or fault on the material of the pipeline during the acoustic monitoring process of the pipeline by means of an interpolation process.

The present invention is now illustrated with reference to the drawings of the enclosed figures which represent an illustrative and non-limiting embodiment, and wherein.

Figure 1:
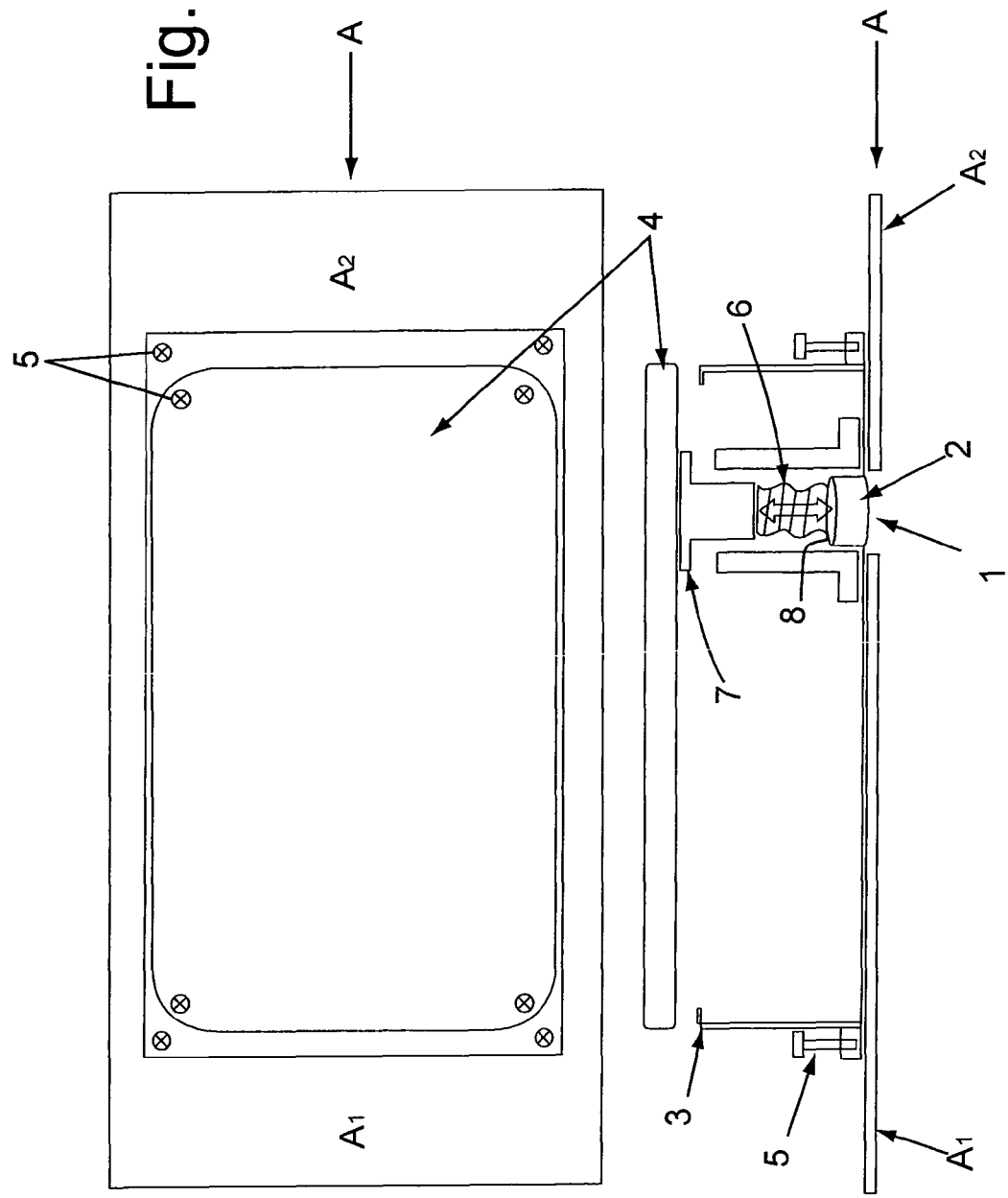
FIG. 1 represents a transversal sectional view of the detection device containing a sensor and a view thereof from above.

With reference to the drawings, the supporting plate A has a pass-through opening 1 in which a sensor 2, e.g. an acoustic sensor/transducer, a piezoelectric acoustic sensor/transducer, a fiber optic sensor, or an accelerometer, is inserted. The containment box 3, equipped with a sealing top 4 is fixed above the plate A by means of fixing elements such as screws 5. The sealing top 4 is also fixed to the containment box by means of screws 5.

In order to avoid possible detachment of the sensor from the metallic surface of the pipeline on which it is situated, due to possible unexpected movements of the pipeline, the compression spring 6 is positioned above the sensor, which is pushed against the same sensor by the piston 7 when the top 4 is fixed on the containment box 3.

Figure 5:
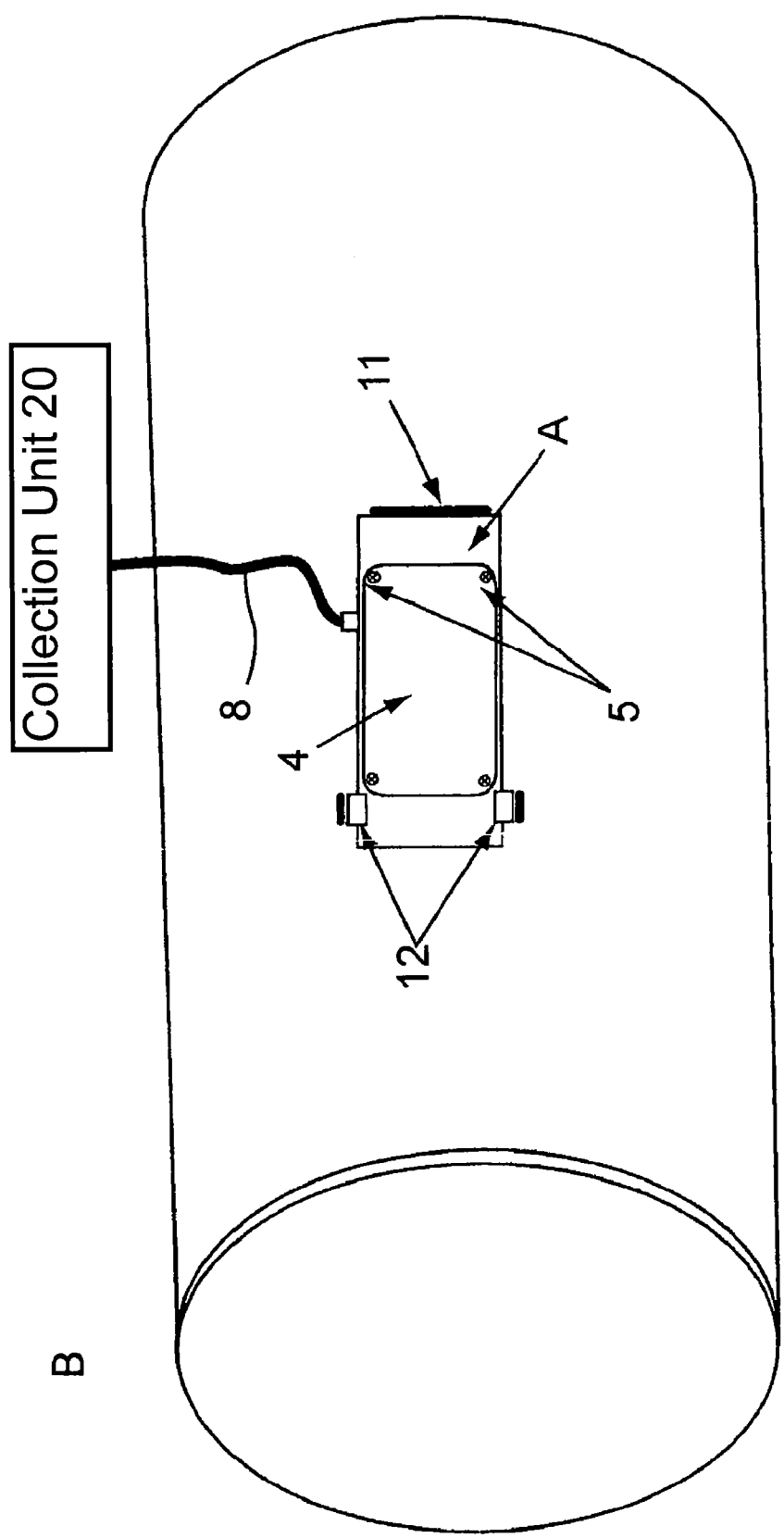
FIG. 5 is a side view of a pipeline on which the overall detection device is fastened by means of the blocking system of FIG. 4.

When the sensor detects an acoustic wave, for example generated by a formation of a new critical fault (crack) or by the development of a fault already under control, the associated acoustic wave (ultrasound) is revealed by the sensor/transducer, transformed into an electric signal by conventional electronics, not illustrated for the sake of simplicity in FIG. 1, and transferred to an external collection centre 20 (illustrated in FIG. 5) by means of the electric wire 8. The collection centre 20 transforms the signal from analogical to digital and transmits it to remote, to the final control and monitoring station.

The supporting plate A has two shapings A1 and A2, at the ends, which serve, in one case, for fixing the device onto the pipeline.

Figure 2:
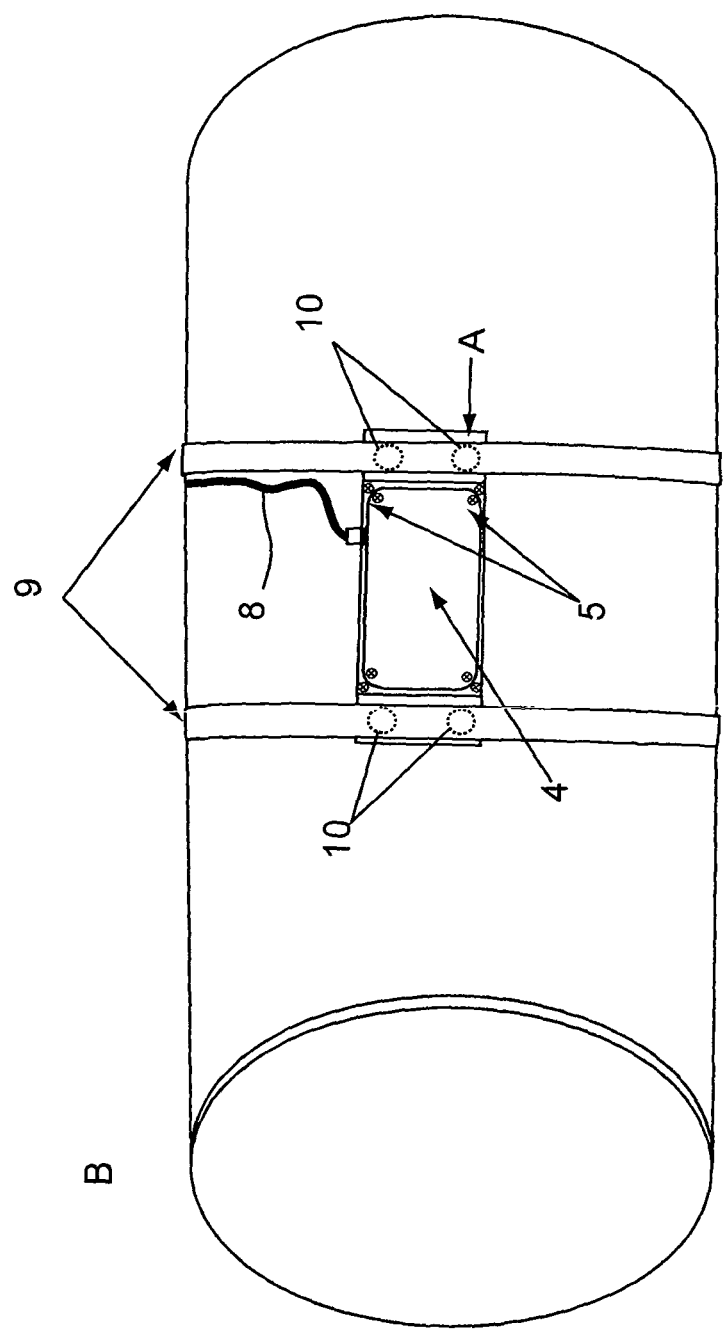
FIG. 2 is a side view of a pipeline on which the overall detection device is fastened by means of fixing belts.
Figure 3:
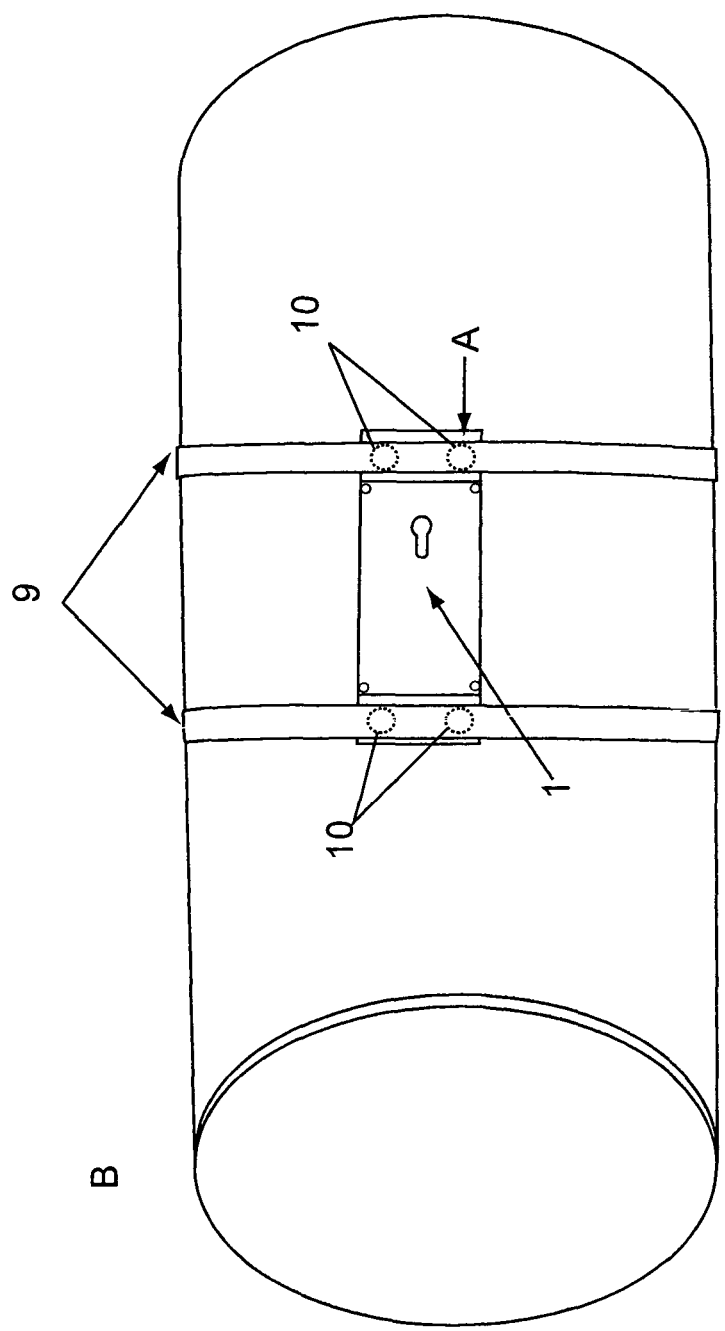
FIG. 3 represents the same view as FIG. 2 with the exception that the top of the device and the sensor have been eliminated.

FIG. 2 illustrates the pipeline B on which the device, object of the present invention, containing the sensor and associated electronics, is fixed by means of the fixing belts 9 which block the supporting plate A by engagement on the parts A1 and A2. The fixing system is better illustrated in FIG. 3 which shows the supporting plate alone fastened by means of the belts. In order to guarantee certain elasticity to the fixing system, spring elements 10 are inserted between the belts 9 and the parts A1 and A2 of the supporting plate.

Figure 4:
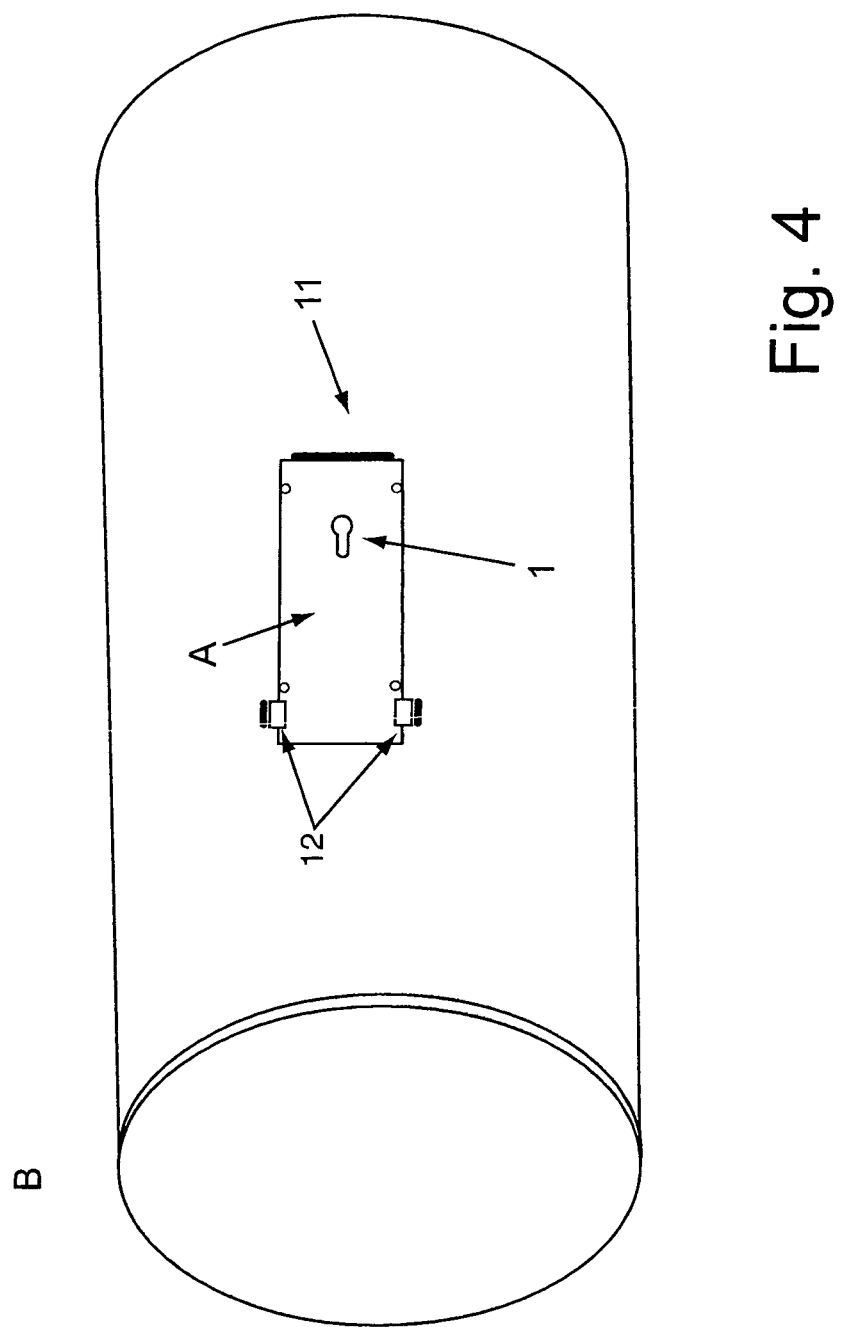
FIG. 4 is the same as FIG. 3 except that it represents a different blocking system of the plate.

FIG. 4 illustrates an alternative method for fixing the detection device of acoustic waves, object of the present invention. The plate A is welded, in correspondence with the edge 11, to the pipeline, whereas the plate is contained by the two L-shaped flanges 12 welded only onto the pipeline, in correspondence with the opposite edge. In this way, the plate A can slide longitudinally, by deformation, without there being any side or vertical movements prevented by the two flanges 12. The sensor/transducer, the associated electronics and the covering box can therefore be inserted on the plate thus fastened, obtaining the situation represented in FIG. 5.

The invention claimed is:

1. A method for the elastic installation on pipelines of a detection device containing an acoustic sensor, which comprises:
   i. arranging a substantially rectangular, steel supporting plate, equipped with a pass-through opening, on the pipeline;
   ii, supporting the sensor on the plate, in correspondence with the pass-through opening, together with associated electronics;
   iii. welding one of the two edges of the plate, orthogonal to a longitudinal axis of the pipeline, onto the same pipeline and withholding the parallel sides, to the longitudinal axis of the pipeline, of the supporting plate between two overturned L-shaped flanges and welded onto the pipeline in correspondence with the other orthogonal edge;
   iv. covering the sensor and the associated electronics with a protection box, equipped with a top, which is adapted to the plate;
   v. positioning a blocking spring between the sensor and the internal top of the box; and
   vi. fixing the box to the supporting plate.

2. The method according to claim 1, wherein the top of the box is integral, not separable from the walls of the box or can be extracted and fixed, under sealing conditions, to the walls of the box by means of fixing devices.

3. The method according to claim 1, wherein the sensor is selected from a piezoelectric acoustic sensor/transducer, a fiber optic sensor, and an accelerometer.

4. The method according to claim 1, wherein a plurality of acoustic sensors are positioned in correspondence with potentially critical sections of the pipeline for the formation of faults.

5. The method according to claim 1, wherein a plurality of acoustic sensors are positioned on a length of 800-1500 m of pipeline, at distances from each other ranging from 10 to 50 m.

6. A method for the elastic installation on pipelines of a detection device containing an acoustic sensor which comprises:
   i. arranging a substantially rectangular, steel supporting plate, equipped with a pass-through opening, on the pipeline;
   ii. supporting the acoustic sensor on the plate, in correspondence with the pass-through opening, together with associated electronics;
   iii. fastening the supporting plate to the pipeline by means of two belts which are engaged on shaped parts of the plate and which are pulled around the pipeline;
   iv. covering the acoustic sensor and the associated electronics with a protection box, equipped with a top, which is adapted to the plate;
   v. positioning a blocking spring between the acoustic sensor and the internal top of the box; and
   vi. fixing the box to the supporting plate,
   wherein at least two spring elements are positioned between the belt and each shaped part of the two edges of the plate respectively, which guarantee that the plate will follow the radial movements of the pipeline when subjected to radial deformations.

7. A detection device supporting sensors suited to monitor a pipeline, comprising:
   x1. a substantially rectangular steel supporting plate, equipped with a pass-through opening;
   x2. an acoustic sensor inserted in said opening;
   x3. electronics associated with the sensor for producing an electric signal;
   x4. a covering top;
   x5. a containment spring positioned between the sensor and the top for holding the same transducer in position, in the pass-through opening; and
   x6. a small piston situated between the top and the spring to favour the thrust of the latter against the sensor.

8. The device according to claim 7, also comprising means for transferring the electric signals to a collection unit for their transformation into digital signals.

9. The device according to claim 7, wherein the sensor is selected from a piezoelectric acoustic sensor/transducer, a fiber optic sensor, and an accelerometer.

* * * * *